United States Patent
Saulnier

(10) Patent No.: US 10,606,451 B2
(45) Date of Patent: Mar. 31, 2020

(54) LOCATION-BASED HEALTHCARE COLLABORATION, DATA MANAGEMENT AND ACCESS CONTROL

(71) Applicant: Michael S. Saulnier, Acton, MA (US)

(72) Inventor: Michael S. Saulnier, Acton, MA (US)

(73) Assignee: IMPRIVATA, INC., Lexington, MA (US)

( * ) Notice: Subject to any disclaimer, the term of this patent is extended or adjusted under 35 U.S.C. 154(b) by 399 days.

(21) Appl. No.: 15/838,474

(22) Filed: Dec. 12, 2017

(65) Prior Publication Data
US 2018/0113582 A1 Apr. 26, 2018

Related U.S. Application Data

(63) Continuation of application No. 14/945,621, filed on Nov. 19, 2015, now Pat. No. 9,846,525.

(60) Provisional application No. 62/081,820, filed on Nov. 19, 2014, provisional application No. 62/183,793, filed on Jun. 24, 2015.

(51) Int. Cl.
| | | |
|---|---|---|
| *H04W 64/00* | (2009.01) | |
| *G06F 3/0482* | (2013.01) | |
| *H04L 29/08* | (2006.01) | |
| *H04W 4/029* | (2018.01) | |
| *G16H 40/20* | (2018.01) | |
| *G16Z 99/00* | (2019.01) | |
| *G06Q 50/22* | (2018.01) | |
| *H04L 29/06* | (2006.01) | |
| *H04W 4/02* | (2018.01) | |
| *H04W 4/33* | (2018.01) | |
| *G16H 40/67* | (2018.01) | |
| *H04W 12/00* | (2009.01) | |
| *H04W 60/04* | (2009.01) | |
| *H04W 12/06* | (2009.01) | |

(52) U.S. Cl.
CPC .......... *G06F 3/0482* (2013.01); *G06Q 50/22* (2013.01); *G16H 40/20* (2018.01); *G16H 40/67* (2018.01); *G16Z 99/00* (2019.02); *H04L 63/08* (2013.01); *H04L 67/12* (2013.01); *H04L 67/18* (2013.01); *H04L 67/22* (2013.01); *H04W 4/023* (2013.01); *H04W 4/029* (2018.02); *H04W 4/33* (2018.02); *H04W 64/00* (2013.01); *H04W 12/00503* (2019.01); *H04W 12/06* (2013.01); *H04W 60/04* (2013.01)

(58) Field of Classification Search
CPC ..... H04W 64/00; H04W 4/043; H04W 60/04; H04W 12/06; H04L 67/18; H04L 67/12; H04L 63/08; H04L 41/22; H04L 67/22; G06F 3/0482; G16H 40/67; G06Q 50/22
See application file for complete search history.

(56) References Cited

U.S. PATENT DOCUMENTS

| | | |
|---|---|---|
| 8,798,647 B1 | 8/2014 | Haney |
| 2003/0008670 A1 | 1/2003 | Satoshi |
| 2003/0045305 A1* | 3/2003 | Ogino .................... G01S 19/12 455/456.1 |

(Continued)

*Primary Examiner* — Charles N Appiah
*Assistant Examiner* — Xiang Zhang
(74) *Attorney, Agent, or Firm* — Morgan, Lewis & Bockius LLP

(57) ABSTRACT

The locations of electronic devices in an institutional facility are determined based on interaction with the wireless mobile devices of users who roam though the facility and interact with (or are detected by) the devices.

16 Claims, 2 Drawing Sheets

(56) References Cited

U.S. PATENT DOCUMENTS

| | | | |
|---|---|---|---|
| 2004/0147269 A1 | 7/2004 | Kim | |
| 2006/0149459 A1* | 7/2006 | Matsuura | G01C 21/3679 |
| | | | 701/540 |
| 2008/0133730 A1 | 6/2008 | Park et al. | |
| 2009/0197617 A1* | 8/2009 | Jayanthi | G01C 21/3438 |
| | | | 455/456.2 |
| 2011/0294506 A1 | 12/2011 | Claussen et al. | |
| 2011/0312345 A1 | 12/2011 | Nam | |
| 2014/0162693 A1 | 6/2014 | Wachter et al. | |
| 2014/0248901 A1 | 9/2014 | Johnsson et al. | |
| 2014/0256249 A1 | 9/2014 | Tse et al. | |
| 2015/0057017 A1* | 2/2015 | Moshfeghi | G01S 19/48 |
| | | | 455/456.1 |
| 2015/0341891 A1* | 11/2015 | Pentti | H04W 4/021 |
| | | | 455/456.1 |
| 2016/0142878 A1 | 5/2016 | Saulnier | |

* cited by examiner

LOCATION-BASED HEALTHCARE COLLABORATION, DATA MANAGEMENT AND ACCESS CONTROL

RELATED APPLICATION

This application is a continuation of U.S. patent application Ser. No. 14/945,621, filed Nov. 19, 2015, which claims the benefit of and priority to U.S. Provisional Patent Application Nos. 62/081,820, filed Nov. 19, 2014, and 62/183,793, filed Jun. 24, 2015, the entire disclosures of which are hereby incorporated by reference.

TECHNICAL FIELD

The invention relates generally to healthcare information technology, and in particular to systems and methods for location-based management of data, access control, and clinical collaboration.

BACKGROUND

In a busy healthcare environment, such as a hospital, clinicians roam frequently among patients, floors and buildings. Each time a clinician reaches a new location, she may require access to patient information or other medical data maintained by the facility (or elsewhere). That data may be accessed via a local, typically shared workstation, or via a handheld wireless device, such as a "smart phone" or tablet capable of hosting applications and establishing telecommunications, Internet and/or local intranet connections.

In particular, medical institutions from hospitals to physician practice groups to testing centers maintain diverse electronic medical records (EMR) systems, which collectively form the healthcare information backbone. EMR systems allow clinicians access to medical information maintained in various back-end systems. The typical workflow when a physician interacts with a patient involves first logging onto the computer system, then launching and logging into one or more EMR applications, selecting the right patient record, verifying that the record matches the patient, reviewing results (often from different sources), checking up on medical references, entering orders or prescriptions (e.g., using computerized physician order entry (CPOE) applications and ePrescribing), and/or charting patient progress. All of these activities may involve the same patient but different applications, and in some cases multiple separate applications for a single patient-specific activity.

Moreover, healthcare records are protected by strict privacy laws (such as the Health Insurance Portability and Accountability Act, or HIPAA), regulatory regimes, and institutional access policies. Accordingly, when a clinician moves from place to place, he may be required to log on to a new terminal or device, and because of data-access restrictions, the log-on procedure may involve cumbersome and/or multiple authentication modalities. Depending on system configuration, the clinician may be required to re-launch the applications that were running on the previously used device. Therefore, there is a need for systems that streamline or avoid authentication procedures and provision a workspace for clinicians on the move, and this, in turn, may depend on knowledge of a clinician's physical location within a facility. Knowledge of a particular individual's location may be obtained in various ways, including from the location of a device with which she interacts—assuming, of course that the device location is accurately known. In a large facility, even seemingly "fixed" devices such as workstations can be moved periodically, and mobile workstations obviously change location frequently.

For example, the location of a device may be specified by global-positioning system (GPS) coordinates, and if the node is equipped with a GPS chipset, its location can be updated as it is moved. Unfortunately, many workstations and other devices are not GPS-equipped, and indeed, GPS tracking is not always possible even for devices that are GPS-enabled; for example, GPS often does not work well within buildings.

SUMMARY

Embodiments of the present invention focus on determining the location of computational or other devices with which clinicians interact. These devices, which include workstations, thick or thin client devices, kiosks, and network-connected medical devices are herein referred to collectively as "nodes." in general, a node is able to access, via a network, one or more data stores that include information (e.g., EMR) of interest to clinicians. The term "network" is herein used broadly to connote wired or wireless networks of computers or telecommunications devices (such as wired or wireless telephones, tablets, etc.). For example, a computer network may be a local area network (LAN) or a wide area network (WAN). When used in a LAN networking environment, computers may be connected to the LAN through a network interface or adapter. When used in a WAN networking environment, computers typically include a modem or other communication mechanism. Modems may be internal or external, and may be connected to the system bus via the user-input interface, or other appropriate mechanism. Networked computers may be connected over the Internet, an Intranet, Extranet, Ethernet, or any other system that provides communications. Some suitable communications protocols include TCP/IP, UDP, or OSI, for example. For wireless communications, communications protocols may include IEEE 802.11x ("Wi-Fi"), Bluetooth, Zigbee, IrDa, near-field communication (NFC), or other suitable protocol. Furthermore, components of the system may communicate through a combination of wired or wireless paths, and communication may involve both computer and telecommunications networks. For example, a user may establish communication with a server using a "smart phone" via a cellular carrier's network (e.g., authenticating herself to the server by voice recognition over a voice channel); alternatively, she may use the same smart phone to authenticate to the same server via the Internet, using TCP/IP over the carrier's switch network or via Wi-Fi and a computer network connected to the Internet.

In accordance herewith, GPS information may be obtained opportunistically from GPS-enabled devices carried by individuals who interact with a node. Thus, in a first aspect, the invention pertains to a method of tracking a location of a movable device including a wireless interface for interaction with a wireless mobile device of a user. In various embodiments, the method comprising the steps of receiving, by the movable device, an input from the user; computationally executing an agent program on the movable device, the agent program detecting the user wireless device via the wireless interface; interrogating, by the agent program via the wireless interface, the user wireless device for local GPS coordinates obtained by a GPS chipset of the user wireless device; reporting the local GPS coordinates as a location of the movable device; and storing the reported location in a location database of movable devices.

The agent may be further configured to obtain from the user wireless device, via the wireless interface, at least one authentication credential of the user, e.g., a biometric indicium.

In some embodiments, the wireless interface communicates with the user wireless device via a short-range wireless protocol, thereby ensuring co-location of the user wireless device and the movable device. The movable device may include a user interface and at least one peripheral for interacting with a user, and the input is received via physical interaction between the user and the peripheral to thereby ensure co-location of the user wireless device and the movable device.

The location database may be managed by a location server configured to (i) determine a location-update frequency for the movable device and (ii) cause the agent program to interrogate user wireless devices for GPS coordinates in accordance with the determined frequency.

In another aspect, the invention pertains to a movable electronic device configured for interaction with users. In various embodiments, the movable electronic device comprises a wireless interface for interaction with a wireless mobile device of a user, an input device for receiving input from the user, a processor, and a computer memory storing agent instructions for execution by the processor. The agent instructions, when executed, causes the movable device to detect the user wireless device via the wireless interface, interrogate the user wireless device via the wireless interface for local GPS coordinates obtained by a GPS chipset of the user wireless device, and electronically communicate the local GPS coordinates for storage in a location database of movable devices.

In some embodiments, the agent instructions further cause the movable device to obtain from the user wireless device, via the wireless interface, at least one authentication credential of the user. e.g., a biometric indicium. The wireless interface may implement a short-range wireless protocol, thereby ensuring co-location of the user wireless device and the movable device.

In various embodiments, the device further comprises a display and at least one peripheral for interacting with a user. The input is received via physical interaction between the user and the peripheral to thereby ensure co-location of the user wireless device and the movable device. In some embodiments, the agent instructions interrogate user wireless devices for GPS coordinates in accordance with a location-update frequency periodically received from a location server.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment." or "an embodiment" in various places throughout this specification are not necessarily all referring to the same example. Furthermore, the particular features, routines, steps, or characteristics may be combined in any suitable manner in one or more examples of the technology. As used herein, the terms "approximately" and "substantially" mean±10%, and in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1:
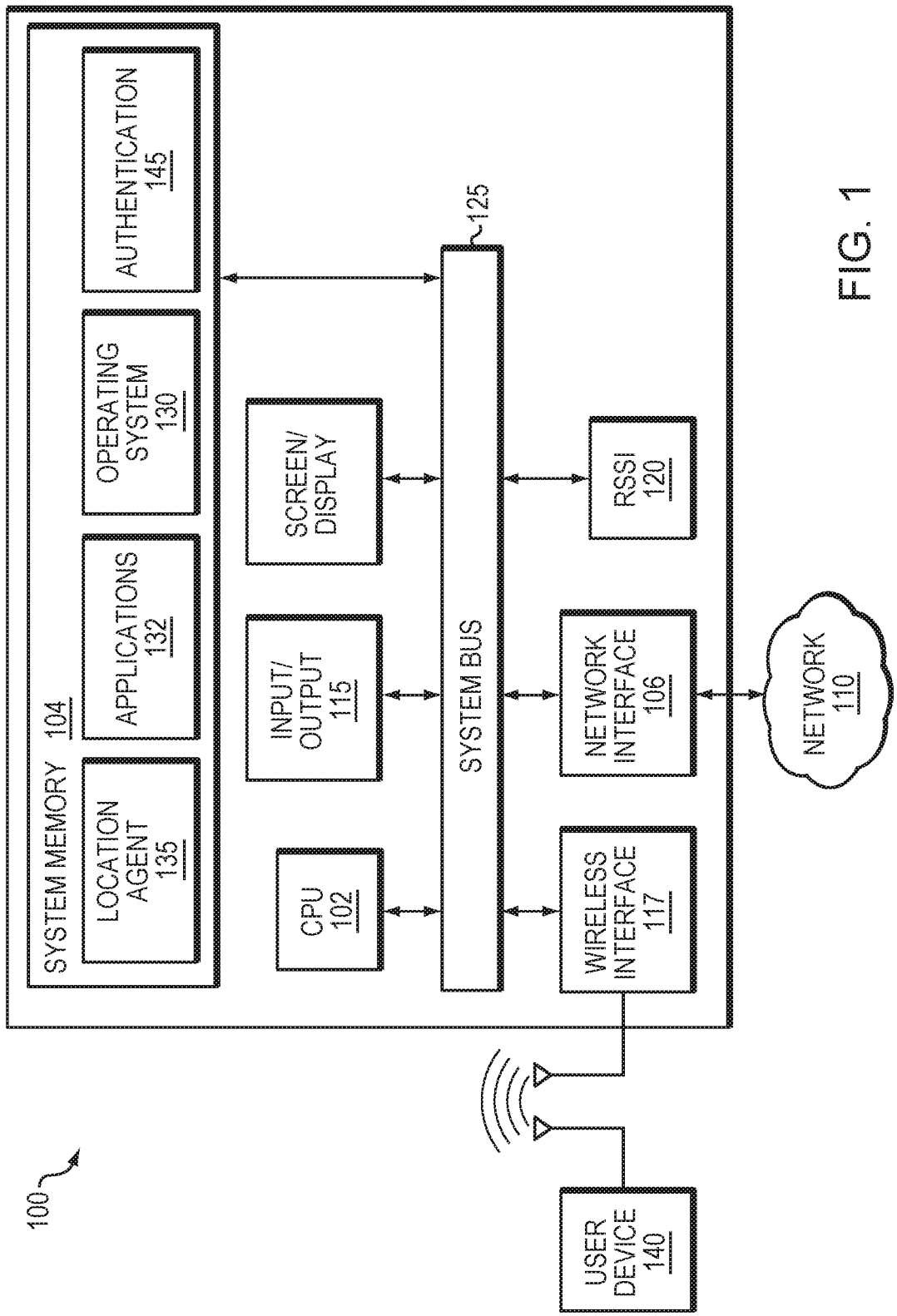
FIG. 1 schematically illustrates a node in accordance with embodiments of the invention.

Refer first to FIG. 1, which illustrates a representative node 100. The node 100 may be a workstation (e.g., a general-purpose personal computer running suitable software), a thick or thin client device, a kiosk, a network-connected medical device, or any other device with which clinicians and other users interact, and which may be moved from time to time within an institutional setting. Node 100 typically includes a processor 102 (e.g., a CPU microprocessor) and associated system memory 104, a network interface 106 (for connection to the institutional network 110 and/or the Internet), and, usually, one or more non-volatile digital storage elements (such as a hard disk, CD, DVD, USB memory key, etc.) and associated drives. Further, workstation 100 includes user input/output devices such as a display screen 112 and conventional tactile input devices 115 such as keyboard and mouse or touch pad. A wireless interface 117, which may be separate from or implemented within network interface 106, facilitates wireless communication with user mobile devices. In some embodiments, workstation 100 includes a received signal-strength indication (RSSI) circuit 120, which, again, may be implemented within or separate from the wireless interface 117. The various components communicate with each other via one or more buses 125.

In use, processor 102 executes one or more computer programs (conceptually illustrated as program modules) stored in system memory 104. An operating system 130 (such as, e.g., MICROSOFT WINDOWS, UNIX, LINUX, iOS, or ANDROID) provides low-level system functions, such as file management, resource allocation, and routing of messages from and to hardware devices (such as I/O device(s) 115) and one or more higher-level user applications 132 (such as EMR applications, office programs, a web browser, etc.). The user interacts with the application(s) 132 by providing input via the input devices, e.g., by typing on the keyboard, moving the mouse, or clicking with the mouse on a displayed control element such as a scroll bar.

A location agent 135 receives data relevant to the presence or proximity of a user (and/or the proximity of a wireless device 140 of the user) and additional data, the nature of which depends on the particular embodiment, relevant to location determination. The wireless devices 140 may be or include, for example, an APPLE IPAD, a SAMSUNG GALAXY, a WINDOWS tablet, or any other type of tablet with wireless communication capability, an APPLE IPHONE, a SAMSUNG GALAXY, or any other "smart" phone (capable of executing on-board "apps" and, typically, of communicating via the telecommunications infrastructure as well as short-range protocols such as WiFi and Bluetooth); as well as laptops and other devices, such as "smart" watches, capable of communicating via a short-range protocol with a more powerful device such as a tablet or smart phone. Wireless interface 117 may communicate with a user's wireless device 140 via a short-range wireless protocol such as Bluetooth, NFC, or WiFi.

In some implementations, node 100 includes an authentication agent 145 that allows a user to obtain access to restricted data consistent with his privilege level and the security policies of the institution. Authentication agents are known in the art and described, for example, in U.S. Ser. No. 11/294,354, filed Dec. 5, 2005, the entire disclosure of which is hereby incorporated by reference.

Figure 2:
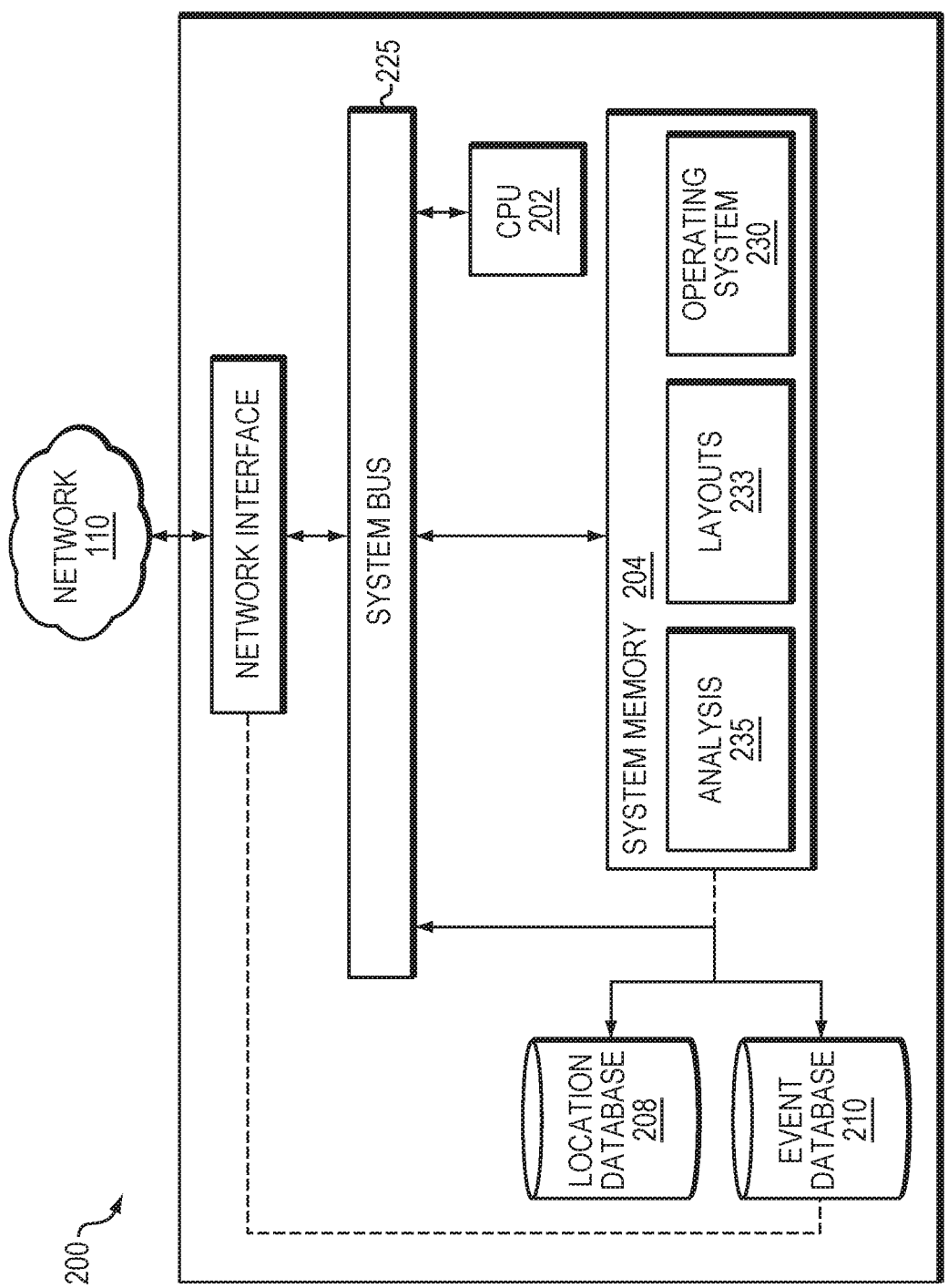
FIG. 2 schematically illustrates a server in accordance with embodiments of the invention.

FIG. 2 illustrates a location server that also typically includes a processor 202 (e.g., a CPU) and associated system memory 204, a network interface 206, a system bus 225, and one or more non-volatile digital storage elements including a location database 208 and an event database 210. The databases 208, 210 may be stored locally as separate files or disk partitions, or may be stored remotely and accessed via network interface 206. Location database 208 stores records each specifying a node and its most recently determined location, as well as, typically, its distance from other nodes.

System memory 204 includes stored instructions defining an operating system 230 and high-level applications (not shown). In addition, memory 204 may store digital representations 233 of one or more physical layouts—e.g., floor plans—of the institution(s) in which nodes 100 are deployed. That is, location server 200 may be located within a single institution or may manage location services for a plurality of institutions. In the latter case, server 200 may store layout information for all institutions in nonvolatile storage and retrieve appropriate files in response to events as described below. An analysis program 235 implements various location-determination functions, also as described below. These functions include analysis of distance and available paths between nodes and obstructions defining the paths in accordance with layout files 233, which are stored in a format subject to this analysis.

More generally, server 200 may be implemented on any suitable computing platform including a processing unit, a system memory, and a system bus that couples various system components including the system memory to the processing unit. During operation, the system memory contains the instructions implementing the functionality described herein. Computers typically include a variety of computer-readable media that can form part of the system memory and be read by the processing unit. By way of example, and not limitation, the system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RAM typically contains data and/or program modules that are immediately accessible to and/or presently being operated on by processing unit. The data or program modules may include an operating system, application programs, other program modules, and program data. The operating system may be or include a variety of operating systems such as Microsoft WINDOWS operating system, the Unix operating system, the LINUX operating system, the Xenix operating system, the IBM AIX operating system, the Hewlett Packard UX operating system, the MACINTOSH operating system, the APACHE operating system, an OPENSTEP operating system or another operating system of platform.

1. GPS-Based Location Determination

Location database 208 may specify a node's location in terms of a room or work area, in terms of absolute (e.g., GPS or other spatial) coordinates, or both. In various embodiments, database 208 maintains a table relating absolute coordinates to informal or named locations meaningful on an institutional level. In this way, if GPS coordinates are specified for a node, the node's record in database 208 can be updated to specify the institutional location. In accordance with embodiments of the present invention, the GPS location of a node is obtained when a user is detected by (e.g., authenticates herself to) the node via a GPS-equipped device 140 using a short-range wireless protocol.

For example, a user may establish a wireless communication channel with the node 100 using a mobile device 140 for purposes of authentication, following an authentication protocol prescribed by the institution's security policy. Authentication agent 145 runs a security process that handles the authentication sequence; this may involve communication with a remote server (e.g., a server that verifies password or biometric information obtained and transmitted by the node). The user's mobile device 140 may run a specialized application for communicating with authentication agent 145 and, for example, obtaining from the user an authentication credential such as a biometric indicium—e.g., reading a fingerprint from the user's thumb when pressed on the device's touchscreen, or reading a vein pattern. During the authentication sequence, location agent 135 obtains GPS data from device 140. (Of course, the functions of agents 135, 145 can be performed by a single application.)

In other implementations, an application running on the user device 140 permits location agent 135 to access GPS information of device 140 whenever communication with the device can be opportunistically established. For example, wireless interface 117 may operate as an NFC reader, which "wakes up" when device 140 is in communication range (e.g., is "woken up" by an NFC tag chip on device 140). Most mobile devices permit their owners to prevent wireless provision of location information, but the device 140 may include an application that is activated when peer-to-peer communication is established with a location agent 135, which the user has given persistent permission to provide (or to allow location agent 135 to access) GPS information during such a peer-to-peer session.

In various embodiments, the conditions under which location agent 135 interrogates the user devices 140 for GPS coordinates are constrained. In some cases, agent 135 may be programmed to always request GPS information from any device 140 with which it establishes communication, following which the GPS coordinates are sent to location server 200. If the node is unlikely to be moved frequently, however, the agent may be programmed to request GPS coordinates only periodically; a highly utilized workstation that is rarely moved, for example, need not have its location updated many times a day as different users log on. Thus, agent 135 may be programmed to obtain GPS coordinates from the next available user device only once during a fixed interval (e.g., a day or a week). Alternatively, agent 135 may operate adaptively based on how often it is moved (i.e., how often the GPS coordinates change from one reading to the next), gradually adjusting the frequency with which new coordinates are obtained to conform to a time-average interval between observed changes. In other embodiments, agent 135 is programmed to request GPS coordinates when it receives an instruction to do so from, for example, location server 200. For example, the node server, rather than agent 135, may keep track of how often devices are moved and set the corresponding update frequencies accordingly.

2. Location Determination without GPS

GPS tracking is not always possible even for devices that are GPS-enabled; for example, GPS often does not work well within buildings. Therefore, in some embodiments, relative spatial locations among a group of nodes are determined based on patterns of user interactivity. These relative spatial locations may suffice in themselves for some purposes, and can also be used to infer absolute spatial coordinates. For example, various implementations may leverage the fact that a user will access more than one node during her workday, and that users tend to walk directly from node to node at approximately the same speed. This type of analysis may be assisted by information obtained from wearable fitness monitors that track, for example, velocity and number of steps taken as explained below.

In one particular implementation, location server 200 monitors user accesses to the various nodes in a facility, and follows the path of each user from node to node as the user approaches or logs on to, and subsequently departs from, a node. For each user, location server 200 computes the amount of time elapsed between successive interactions with (i.e., "proximity events" at) different nodes. Any of various interactions can qualify as a proximity event, depending on device capabilities and implementation preferences. Most simply, a proximity event involves physical interaction between a user and a node 100, e.g., a log-on attempt. In some embodiments, however, the user's presence is detected wirelessly, e.g., a proximity event may be a wireless communication between a node and a user wireless device, generally over a short-distance link; the wireless communication may be detection of the device by NFC or Bluetooth reader circuitry in wireless interface 117. In this way, the user need not interact physically with node 100 to be registered as co-located with the device; and because several people may be in proximity to a device being used by only one person, this approach enables simultaneous tracking of more people and their paths.

Similarly, departure of a user from a node 100 can involve physical interaction (typically the last event or activity registered for the user on the node, e.g., log-off) or moving out of wireless communication range. For accurate time measurements, of course, the same type of proximity event (log-on/log-off, duration of wireless detection) should be used for the arrival and departure events that define an estimated user path between nodes. Because each node 100 typically reports only its own proximity events, it is server 200 that identifies the transitions corresponding to a single individual's travel from one node to another. Because database 210 can be queried by user, it is straightforward to trace any particular user's node transitions and thereby identify the previous node visited.

The elapsed time between a single individual's proximity events at different nodes, if analyzed properly, can indicate the distance between the two nodes, particularly when corroborated by similar proximity events of other individuals. For example, a table of proximity events in event database 210 may contain the following illustrative entries:

|        | Node 1 | Node 2 | Node 3 | Node 4 |
|--------|--------|--------|--------|--------|
| Node 1 | X      | 1:05:02 |        |        |
|        |        | 0:0:32 |        |        |
|        |        | 0:13:12 |        |        |
| Node 2 | 1:05:02 | x      |        |        |
|        | 0:0:32  |        |        |        |
|        | 0:13:12 |        |        |        |
| Node 3 |        |        | x      |        |
| Node 4 |        |        |        | x      |

In the following discussion, cells are referenced by row/column. In the node 2/node 1 cell (and the corresponding node 1/node 2 cell), the first line of the entry indicates successive proximity events for the same individual at nodes 1 and 2 (and no intervening nodes), and the elapsed time between departure from (e.g., the last activity performed on) node 1 and arrival at (e.g., the first activity performed on) node 2—or vice versa, since the order is generally irrelevant—was 1:05:02. The second line indicates that a single individual—who may or may not be the person whose accesses were recorded on the first line—successively accessed nodes 1 and 2 with 32 seconds elapsing between last and first events, respectively, on these nodes. Since this is the minimum amount of time in the cell, it can in appropriate circumstances be considered the approximate travel time between nodes 1 and 2 (since longer times typically will reflect diversions or interruption). What circumstances are appropriate may depend on a desired confidence level, which may itself depend on the number of entries in the cell and/or corroboration among entries. For example, suppose the cell contains few entries but the two or three smallest elapsed times are approximately the same; these similar times corroborate each other and increase the likelihood of a valid result.

To estimate the distance between nodes once an acceptable elapsed-time minimum is identified, various factors may be taken into account—e.g., the average walking speed of users in the institution, the average interval between a last recorded event at a node and when the user actually departs, and the average interval between arrival at a new node and the first recorded event thereon. Although walking speeds can vary greatly depending on a multitude of factors such as height, weight, age, terrain, surface, load, culture, effort, and fitness, the average human walking speed is about 5.0 kilometers per hour or about 3.1 miles per hour.

Once successive proximity events are detected and, if necessary, adjusted as described above, they can be used to compute the approximate distance between the corresponding nodes. For example, if the proximity events involve physical interaction with a node, the above-noted access and departure intervals may be subtracted from the average of the recorded minimum times between successively accessed nodes, and the result multiplied by the average walking speed to obtain a distance estimate. Because the expected departure and arrival intervals and the expected gait are averaged values, accuracy will be improved by using multiple identified minimum times (rather than a single identified time) between successive proximity events, since longer times reflect extraneous factors such as interruptions. It should be understood that any suitable approach to unsupervised learning of the distance between nodes may be employed so long as it accounts for such sources of "noise."

In some embodiments, location agent 135 is programmed to interact (i.e., sense and exchange data) with fitness tracking devices via wireless interface 117. These devices track physical activities such as, critically, the number of steps taken or distance covered on foot. With this information it is not necessary to estimate elapsed time based on proximity events at two nodes in order to determine the distance between those nodes. For example, location agent 135 may be programmed to wirelessly check for a fitness device when a user logs in at, or comes within communication range of, a node. If one is found, the agent may download recent activity—e.g., number of steps and average walking speed during the user's last change of location, or, if available, distance covered. When location agent 135 has successfully obtained this data, it may provide it to location server 200. The server 200, in turn, may look up the previous node accessed by the user, thereby providing a direct distance entry, i.e., one that need not be converted based on time and estimated gait. This distance still may not correspond to the actual distance between nodes, since the wearer of the fitness device may not have followed a direct path to the reporting node from the previous node. Once again, consistency among multiple entries, floorplan constraints and/or fitness tracking entries indicating directional changes may be used to identify and eliminate spurious database entries.

It is further possible to sense the presence of a user at a node based on an observed wireless signal strength, rather than in response to log-in or communication event. For example, RSSI 120 can determine the strength of signals in the immediate environment, and if any of these is sufficiently strong to indicate close proximity of the transmitting device, co-location of the registered owner of that device may be inferred. Agent 135 can operate RSSI 120 and detect transitions, i.e., the appearance of a user device when signal strength reaches a threshold level indicative (given the known parameters of the sensed wireless protocol) of close proximity, and the departure of the user from the node when the previously detected, above-threshold signal strength falls below the threshold. Location agent 135 reports these conditions as arrival and departure proximity events to location server 200.

RSSI 120 can also operate to establish correlations between detected signal strengths and user activity. For example, RSSI 120 can measure signal strength when a user logs on and similarly begin tracking signal strength when the user logs out. Over time, these measured values by user and for each node can determine the proper threshold values for approaching and departing users. Further, signal strength can be measured as RSSI 120 detects its peer nodes within range, since all nodes have a wireless interface 117, RSSI 120 and a location agent 135. The measured node-to-node signal strengths can be used to build graph of RSSI dividing boundaries between adjacent nodes. This information, together with the measured approach/departure signal strength, can more accurately determine when a user is approaching or leaving a node.

Since wireless interface 117 can both transmit and receive, ranging can involve the cooperation of the node 100 and the user's device 140. For example, location agent 135 may modulate the transmission power of wireless interface 117, progressively reduce transmission power until it the user's device 140 can no longer detect it. This ranging scheme can be run continuously to determine if the user is approaching or departing from the node 100 based on the monitored transmission power over time. If the user is approaching, the minimum power needed to contact the user's device over time will continue to drop until a lower threshold is reached. Monitoring many devices 140 and correlating them with users who actually logged in will provide a characteristic transmit power boundary to establish who is "close" to the node.

Once the distances between nodes are established, they are stored in location database 208 and can be used to determine the absolute spatial coordinates of the nodes 100 if those coordinates are known for a few of the nodes. Indeed, depending on the degree of knowledge of the institution's interior layout, it may be possible to deduce the institutional or absolute spatial locations of all nodes even if no absolute location coordinates are known in advance, simply by optimizing the fit between observed inter-node distances and the constraints imposed by the known geometry; that is, given enough inter-node distances, there may be only one arrangement of nodes that is physically possible given the stored layout 233. Conventional dynamic-programming techniques and optimization algorithms are available to perform this analysis without undue experimentation. Suitable approaches are described in, for example, Addesso, Bruno & Restaino, "Adaptive localization techniques in wifi environments," 5*th IEEE International Symposium on Wireless Pervasive Computing* 289-294 (2010); Altini, Brunelli, Farella & Benini, "Bluetooth indoor localization with multiple neural networks," 5*th IEEE International Symposium on Wireless Pervasive Computing* 295-300 (2010); Almaula & Cheng, "Bluetooth triangulator," Tech. rep., Department of Computer Science and Engineering, University of California, San Diego (2006); Yoo & Kim, "Target Localization in Wireless Sensor Networks Using Online Semi-Supervised Support Vector Regression," 15 *Sensors* 12539-12559 (2015); and Reddy & Veloso, "RSSI-based physical layout classification and target tethering in mobile ad-hoc networks," *Proceedings of the* 2011 *IEEE/RSJ International Conference on Intelligent Robots and Systems* 2327-2332 (2011), the entire disclosures of which are hereby incorporated by reference.

Any suitable programming language may be used to implement without undue experimentation the functions described above, including those of location agent 135, with processing responsibility allocated between node 100 and server 200 as desired by the system designer. Illustratively, the programming language used may include assembly language, Ada, APL, Basic, C, C++, C*, COBOL, dBase, Forth, FORTRAN, Java, Modula-2, Pascal, Prolog, Python, REXX, and/or JavaScript, for example. Further, it is not necessary that a single type of instruction or programming language be utilized in conjunction with the operation of the system and method of the invention. Rather, any number of different programming languages may be utilized as is necessary or desirable.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A server for managing locations of movable electronic devices, the server comprising:
    a processor;
    a network interface for communicating with movable electronic devices that are incapable of receiving GPS signals;
    a location database comprising records each specifying a movable electronic device and its location;
    a computer memory storing instructions for execution by the processor, the instructions, when executed, (i) determining update intervals for movable electronic devices, (ii) in accordance with each determined update interval, instructing a movable electronic device to (a) interrogate a portable wireless mobile device for GPS coordinates only upon occurrence of a proximity event when the portable wireless mobile device is moved into proximity to the movable electronic device, and (b) report the GPS coordinates as a location of the movable electronic device, and (iii) storing the reported location in the location database.

2. The server of claim 1, wherein each update interval corresponds to an adaptive time period based on a frequency with which the location of the movable device changes.

3. The server of claim 1, wherein the location database is a remote database accessible via the network interface.

4. The server of claim 1, further comprising non-volatile storage for local storage of the location database.

5. A system for tracking and updating a location of movable electronic devices, the system comprising:
    a location database comprising records each specifying a movable electronic device and its location;
    a location server comprising:
        a first processor,
        a network interface for communicating with a movable electronic device, and
        a first computer memory storing instructions for execution by the first processor, the instructions, when executed, (i) determining an update interval for the movable electronic device, (ii) in accordance with the determined update interval, requesting an updated location from the movable electronic device, and (iii) storing the updated location in the location database; and
    a movable electronic device that is incapable of receiving GPS signals, the movable electronic device comprising:
        a wireless interface for interaction with portable wireless mobile devices of users,
        an input device for receiving input from the users,
        a second processor, and
        a second computer memory storing agent instructions that, when executed by the second processor, cause the movable electronic device to (i) opportunistically trigger a communication session with a portable wireless mobile device only upon occurrence of a proximity event when the portable wireless mobile device is moved into proximity to the movable electronic device, (ii) interrogate the portable wireless mobile device via the wireless interface during the session for local GPS coordinates of the portable wireless device and obtained by a GPS chipset of the portable wireless mobile device, and (iii) electronically communicate the local GPS coordinates to the location server as the updated location of the movable electronic device.

6. The system of claim 5, wherein the update interval corresponds to an adaptive time period based on a frequency with which the location of the movable electronic device changes.

7. The system of claim 5, wherein the location database is a remote database accessible by the location server via the network interface.

8. The system of claim 5, wherein the location server comprises non-volatile storage for local storage of the location database.

9. The system of claim 5, wherein the agent instructions further cause the movable electronic device to obtain from the portable wireless mobile device, via the wireless interface, at least one authentication credential of a user.

10. The system of claim 9, wherein the at least one authentication credential is a biometric indicium.

11. The system of claim 5, wherein the wireless interface implements a short-range wireless protocol, thereby ensuring co-location of the portable wireless mobile device and the movable electronic device.

12. The system of claim 5, wherein the movable electronic device is configured to wake up when the portable wireless mobile device enters a communication range of the movable electronic device.

13. The system of claim 12, wherein the communication range is an NFC range.

14. The system of claim 5, wherein the movable electronic device comprises a display.

15. The server of claim 1, wherein the movable electronic devices lack GPS chipsets.

16. The system of claim 5, wherein the movable electronic device lacks a GPS chipset.

* * * * *